United States Patent [19]

Glotkin

[11] Patent Number: 4,733,410
[45] Date of Patent: Mar. 29, 1988

[54] FINGER COT CONSTRUCTION

[76] Inventor: Ruth E. Glotkin, 5115 Atlantic Ave., Ventnor, N.J. 08406

[21] Appl. No.: 862,302

[22] Filed: May 12, 1986

[51] Int. Cl.⁴ .............................................. A41D 13/08
[52] U.S. Cl. ........................................ 2/21; 66/172 E
[58] Field of Search .................... 2/21, 161 A, 163; 66/170, 172 E; 15/227; D4/103; 128/87 A

[56] References Cited

U.S. PATENT DOCUMENTS

| 883,452 | 3/1908 | Corliss | 2/21 |
| 942,003 | 11/1909 | Marsh | 15/227 |
| 2,129,496 | 9/1938 | Hollingsworth | 2/21 |
| 2,351,906 | 6/1944 | Beatty | 2/21 |
| 2,637,031 | 5/1953 | Friedman | 2/21 |
| 3,263,682 | 8/1966 | Rosenfield | 66/170 X |
| 3,306,288 | 2/1967 | Rosenfield | 66/170 X |
| 3,348,541 | 10/1967 | Loebeck | 2/21 |
| 4,127,222 | 11/1978 | Adams | 2/21 |

Primary Examiner—Harvey C. Hornsby
Assistant Examiner—Joseph S. Machuga
Attorney, Agent, or Firm—Caesar, Rivise, Bernstein, Cohen & Pokotilow, Ltd.

[57] ABSTRACT

A tubular knit finger cot having one end closed by a transverse seam and the other end open, the closed end region tapering toward the seam, and resiliently extensile yarn interknit in the region adjacent to the open end to provide an elastic retaining collar.

1 Claim, 4 Drawing Figures

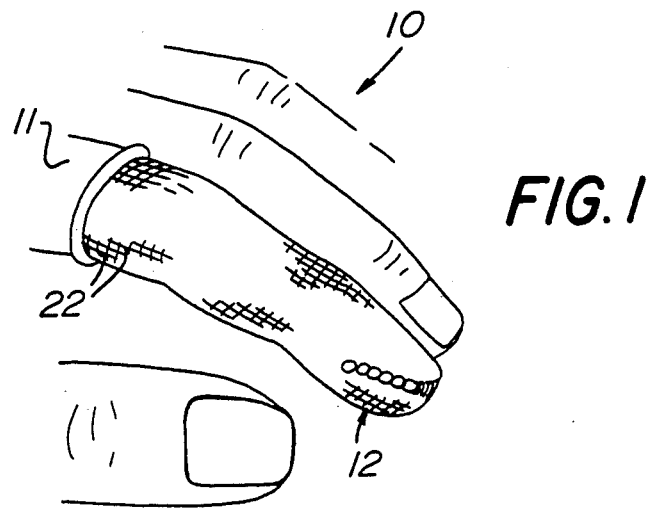
FIG. 1
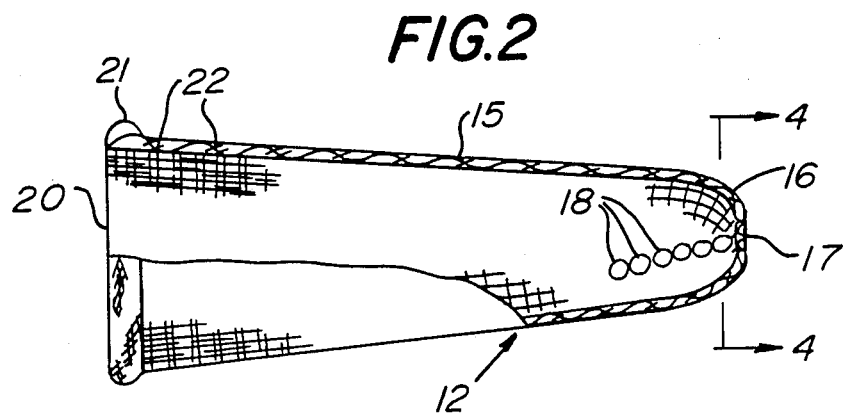
FIG. 2
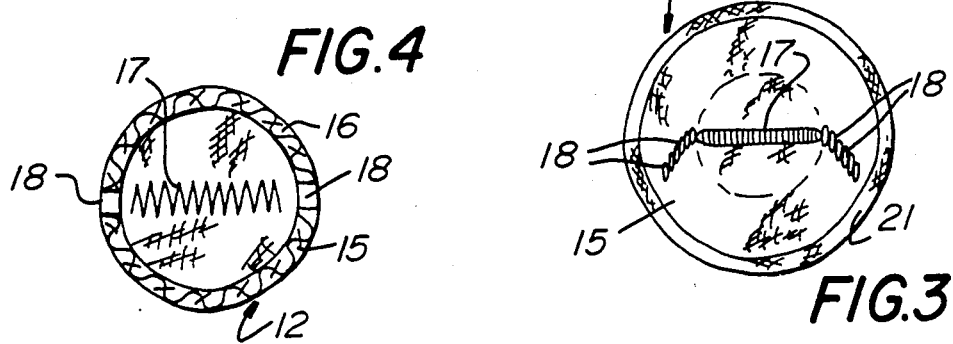
FIG. 4
FIG. 3

FINGER COT CONSTRUCTION

BACKGROUND OF THE INVENTION

While the field of finger cots or stalls is old and highly developed, the prior art finger cots have been lacking in versatility, durability, sensitivity, and have not found broad acceptance in practical use.

The below listed patents illustrate the prior art of which applicant is aware:

| U.S. PAT. NO. | PATENTEE |
| --- | --- |
| 911,838 | NAPIER |
| 1,144,777 | OVER |
| 1,362,461 | ANAST |
| 2,434,317 | GROSS |
| 2,461,872 | BEATTY |
| 2,522,842 | SCHOLL |
| 3,263,681 | NECHTOW ET AL. |
| 3,263,682 | ROSENFIELD |
| 4,507,807 | KARKANEN |

SUMMARY OF THE INVENTION

It is an important object of the present invention to provide a new and improved finger cot construction which is of increased comfort on the user's finger, more securely retained on the finger, relatively inexpensive to manufacture, and which is capable of minor variations to greatly enhance its versatility in use. For example, finger cots of the present invention are admirably well suited for use in handling money, as for accuracy in counting or dispensing while retaining one's fingers clean, similarly for use in fingering or handling new printing or other material while keeping the handled material free of fingerprints, further in handling coins or tokens as in depositing and removing the same with respect to slot machines, and also as a medical bandage or cover for a bandage to prevent contamination of a wound.

Other objects of the present invention will become apparent upon reading the following specification and referring to the accompanying drawings, which form a material part of this disclosure.

The invention accordingly consists in the features of construction, combinations of elements, and arrangements of parts, which will be exemplified in the construction hereinafter described, and of which the scope will be indicated by the appended claims.

BRIEF DESCRIPTION OF THE DRAWINGS

FIG. 1 is a perspective view showing the fingers of a wearer's hand, a finger cot being engaged on one of the fingers.

FIG. 2 is a longitudinal view showing a finger cot of the present invention apart from a wearer's hand, partly broken away to illustrate the interior.

FIG. 3 is an end view of the finger cot of FIG. 2, as from the right hand end thereof.

FIG. 4 is a transverse sectional view taken generally along the line 4—4 of FIG. 2.

DESCRIPTION OF THE PREFERRED EMBODIMENT

Referring now more particularly to the drawings, and specifically to FIG. 1 thereof, a hand is there generally designated 10, including an index finger 11 carrying a finger cot or stall 12, constructed in accordance with the teachings of the present invention. The finger cot 12 is advantageously closely conformably engaged in receiving relation with the finger 11.

As best seen in FIGS. 2-4, the finger cot 12 includes an elongate knit tube 15 fabricated of flexible elongate filamentary material or yarn by tubular knitting. Thus, the knit tube 15 is of generally hollow, cylindrical formation, having one end portion 16 closed by a laterally or diametrically extending seam 17. The end closure or seam 17 closes the outer or distal end of the tube 15, and the tube is of increasing dimension in the direction inwardly from the end closure or seam 17, for snug conformably fitting to a user's finger end portion.

Extending along opposite sides of the tube 15, from opposite ends of the closure seam 17 are a pair of rows or series of aligned vents, apertures or holes 18. The pair of laterally opposed rows of holes 18 afford ventilation and cooling to a wearer's fingers, reducing or obviating the possibility of perspiring and damaging articles being handled.

At the opposite or inner end 20, remote from the closed end portion 16, the tube 15 is open, and there bounded by a circumferential bead or annular thickened formation 21 which may be provided by rolling of the open terminal tube portion.

The finger cot 12 may be entirely of cotton, as for a sterile bandage, or the like; but advantageously there may be interknit with cotton yarn an elastic yarn, as at 22 along a region extending inwardly a predetermined distance from the open tube end 20. The elastic yarn 22 combines with the cotton yarn to define a resiliently extensile band or elastic collar for snug, frictional embracing engagement about a wearer's finger at a location spaced from the distal finger end. This serves to effectively insure retention of the finger cot in position on a wearer's finger during use, without discomfort or other deleterious effects. The elastic yarn may constitute between twenty percent and eighty percent of the cotton yarn in accordance with the desired circumferential resilience and frictional engagement for the particular application. Stated otherwise, the ratio of elastic yarn ends to cotton yarn ends may vary 1:5 to 4:5 to obtain the desired holding effect. By this construction a relatively thin cotton yarn may be employed for high tactile sensitivity of the finger ends, such as 20 denier, single strand yarn. The elastic yarn may be of the type manufactured by DuPont and sold under the trademark Lycra.

From the foregoing it is seen that the present invention provides a finger cot which is adapted for comfortable and convenient use over a long useful life, at a reasonable cost, and which otherwise fully accomplishes its intended objects.

Although the present invention has been described in some detail by way of illustration and example for purposes of clarity of understanding, it is understood that certain changes and modifications may be made within the spirit of the invention.

What is claimed is:

1. A finger cot fabricated of a first yarn and comprising a knit tube, a seam extending in closing relation laterally across one end of said tube, the other end of said tube being open, said tube having a longitudinally inwardly widening end portion extending from said one tube end for snugly receiving the distal end of a wearer's finger, a circumferential bead at said open tube end for retaining engagement with a received finger at a location spaced from the distal finger end, and elastic yarn interknit with said first yarn adjacent to said other tube end along a region extending inwardly a predetermined distance from said open tube end to define an elastic collar for frictional embracing engagement with a wearer's finger, said one end portion of said tube having vent openings on opposite sides thereof, said vent openings being arranged in a row extending longitudinally of said tube from opposite ends of said seam only.

* * * * *